United States Patent
Lorenz et al.

(10) Patent No.: US 8,304,498 B2
(45) Date of Patent: Nov. 6, 2012

(54) MEDICAL DEVICES COMPRISING A MODIFIED POLYAMIDE

(75) Inventors: Günter Lorenz, Tübingen (DE); Tina Schackmann, Marburg (DE); Andreas Greiner, Amöneburg (DE)

(73) Assignee: Abbott Laboratories Vascular Enterprises Limited, Dublin (IE)

( * ) Notice: Subject to any disclaimer, the term of this patent is extended or adjusted under 35 U.S.C. 154(b) by 56 days.

(21) Appl. No.: 12/521,552

(22) PCT Filed: Dec. 28, 2007

(86) PCT No.: PCT/EP2007/011449
§ 371 (c)(1),
(2), (4) Date: Dec. 7, 2010

(87) PCT Pub. No.: WO2008/080613
PCT Pub. Date: Jul. 10, 2008

(65) Prior Publication Data
US 2011/0082263 A1    Apr. 7, 2011

(30) Foreign Application Priority Data
Dec. 29, 2006    (EP) .................................... 06027100

(51) Int. Cl.
C08L 77/00    (2006.01)
A61K 9/00    (2006.01)
A61F 13/00    (2006.01)

(52) U.S. Cl. ........ 525/420; 424/400; 424/422; 424/423; 525/426

(58) Field of Classification Search .................. 525/420, 525/426; 424/400, 422, 423
See application file for complete search history.

(56) References Cited

U.S. PATENT DOCUMENTS

| | | | |
|---|---|---|---|
| 4,120,928 | A | 10/1978 | Furukawa et al. |
| 5,068,284 | A | 11/1991 | Ullman et al. |
| 5,216,087 | A | 6/1993 | Kim et al. |
| 5,932,686 | A | 8/1999 | Hoff |
| 2003/0065107 | A1 | 4/2003 | Lacroix et al. |
| 2010/0217211 | A1 | 8/2010 | Lorenz |

FOREIGN PATENT DOCUMENTS

| | | |
|---|---|---|
| DE | 4301097 | 7/1994 |
| EP | 0275988 | 7/1988 |
| EP | 0600793 | 6/1994 |
| EP | 1783156 | 5/2007 |
| JP | 63037125 | 2/1988 |
| JP | 2006036976 | 2/2006 |
| WO | WO 00/28807 | 5/2000 |
| WO | WO 02/074194 | 9/2002 |
| WO | WO 2004/069780 | 8/2004 |
| WO | WO 2005/076947 | 8/2005 |
| WO | WO 2006/053777 | 5/2006 |
| WO | WO 2008/080613 | 7/2008 |
| WO | WO 2008/138568 | 11/2008 |
| WO | WO 2008/138569 | 11/2008 |
| WO | WO 2008/138570 | 11/2008 |

OTHER PUBLICATIONS

PCT/EP07/11449, May 23, 2009, International Search Report.
U.S. Appl. No. 12/599,275, filed Nov. 6, 2009, Güenter.
U.S. Appl. No. 12/599,277, filed Nov. 6, 2009, Güenter.
International Search Report for WO2008/138570 mailed Sep. 18, 2008.

*Primary Examiner* — Ana Woodward
(74) *Attorney, Agent, or Firm* — Workman Nydegger; Jonathan D. Feuchtwang

(57) ABSTRACT

The present invention refers to medical devices comprising a modified polyamide or to modified polyamides or modified polyamide elastomers with the polyamides having high flexibility and high stress resistance, especially tensile strength or tear resistance, in addition to the good physical characteristics of the known polyamide elastomers.

34 Claims, No Drawings

MEDICAL DEVICES COMPRISING A MODIFIED POLYAMIDE

FIELD OF THE INVENTION

The present invention refers to medical devices comprising a modified polyamide or to modified polyamides or modified polyamide elastomers with the polyamides having high flexibility and high stress resistance, especially tensile strength or tear resistance, in addition to the good physical characteristics of the known polyamide elastomers.

BACKGROUND OF THE INVENTION

Polyamides or polyamide elastomers have been used in the polymer industry for a long time and—due to their enormous range of possible applications—are found in many branches of industrial products. Recently in the area of medicinal devices good use has been made of these materials especially in implants. One of the most important use of polyamide or polyamide elastomers is related to medical balloons, especially in the field of percutaneous transluminal angioplasty (PTA) or percutaneous transluminal coronary angioplasty (PTCA). The most popular polyamides used include different sorts of Nylons or mixed forms such as PEBAX™. Even though these materials have certainly been used successfully, due to the strains put on the materials and the necessity to improve their characteristics in the light of growing experience coming from increasing numbers of treated patients, there clearly is a need for improved materials allowing for an effective treatment of the patient preferably with an economical production process.

SUMMARY OF THE INVENTION

It is an object of the current invention to provide modified polyamides or modified polyamide elastomers having high flexibility and high stress resistance, especially tensile strength or tear resistance in addition to the good physical characteristics of the known polyamide elastomers, especially to accordingly provide medical devices comprising these modified polyamides or modified polyamide elastomers.

The invention thus refers to a medical device or medical devices comprising a polymer producible by contacting/mixing one or more polyamides with an at least mono-substituted α,ω-di-carboxylic acid or its alkyl ester and heating to a temperature above 150° C.

The invention further resides in medical devices comprising a polymer according to general formula IV

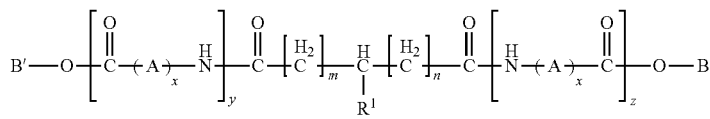

The invention further refers to a polymer producible by contacting/mixing one or more polyamides with an at least mono-substituted α,ω-di-carboxylic acid or its alkyl ester and heating to a temperature above 150° C.

The invention further also resides in a polymer according to general formula IV

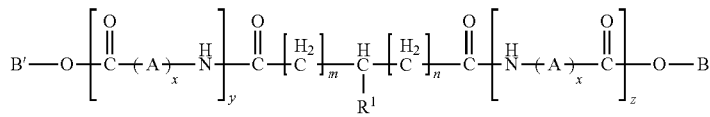

The invention furthermore resides in the use of a polymer according to the invention in the production of medical devices, medical balloons, balloon material, stents, stent grafts, and catheters.

In a further embodiment the invention is directed to a method of treatment of a disease, like a cardiovascular disease, especially a stenosis, using in a patient, being a mammal, especially a human, in need thereof a medical device according to the invention, desirably in minimal invasive surgery like PTCA.

In yet another embodiment the invention is directed to the use of a medical device according to the invention for the treatment of a disease, like a cardiovascular disease, especially a stenosis, especially through minimal invasive surgery like PTCA.

DETAILED DESCRIPTION OF THE INVENTION

The use of stents, balloons, catheters and other medical devices etc. in minimal invasive surgery, especially in the cardiovascular field, has in the last years shown a high growth. As a consequence the need for useful materials fulfilling highly specialized needs in the field of different medicinal devices has clearly risen in a technical area, which traditionally is more governed by bulk products. Especially in the field of vascular balloons there was a clear desire for an elastomer, which is on one hand flexible enough to be introduced into a vascular environment without causing damage, while on the other hand being stable and rigid enough, especially in the moment of actual surgery, inflation in the vessel, to not be extended too much inside the vessel. Besides that, the material should also have a low water absorption, because its physicochemical properties, while used or while on the shelf could be severely hampered by accepting too much water, as it could also be hampered by changes during storage due to thermo-oxidation.

The invention thus refers to a medical device comprising a polymer producible by contacting/mixing one or more polyamides with an at least mono-substituted α,ω-di-carboxylic acid or its alkyl ester and heating to a temperature above 150° C.

In a preferred embodiment of the medical device according to the invention the heating is done
a) already during the mixing/contacting and/or
b) under protective gas atmosphere, preferably under argon and/or
c) to a temperature above 200° C., preferably above 220° C. and/or
d) in 2 steps with different temperatures preferably divided by an intermediate step in which the second temperature is reached within a certain time limit and/or
e) over a time period of more than 3 h, preferably of more than 4 h.

Most preferably of the medical device according to the invention the mixing is done under protective gas atmosphere—preferably under argon—in a first heating step at more than 200° C.—preferably 220° C.—for more than 1 h—preferably 2 h. The temperature was consequently raised within 10 to 30 min—preferably within 20 min—to more than 220° C.—preferably to 250° C.—and the mixture was stirred for another 2 h.

Even though DE 43 01 097 A1 mentions the treatment of a polyamide with methyl adipic acid it is completely silent on medical devices, instead belonging to the field of adhesives.

Currently 3 kinds of material are usually used for medical devices, especially for medical balloons, over which the material of the current invention—if compared case by case—shows advantages.

a) Nylon: Over Nylon, coming in different sorts, especially Nylon-12, the polymers of the invention show the advantage, that they are more flexible and/or have a lower water absorption. Especially the lack of flexibility is often considered as a drawback in medical devices using Nylon.

b) PEBA: Over PEBA (e.g. PEBAX®) the polymers of the invention show the advantage, that they are slightly more rigid and/or have a lower water absorption, again making them superior for the intended special use and allowing a much needed compromise balancing flexibility and rigidity. In addition the material of the invention seem to show higher stability, especially if compared to the effects of thermo-oxidation shown by PEBA and/or also an improved dimensional stability. Also, producing a compound according to the invention needs one polymerization step less than known from PEBA, resulting in the possibility of lower production costs.

c) Blend of a) and b): The need for a compromise between the higher rigidity of Nylon and higher flexibility of PEBA has already resulted in blends being used. Still, these have no defined structures or phases, giving the material of the inventions which seems to have a lower water absorption also already an inherent advantage, whereas on the other hand the material according to the invention lends to the producer also the possibility to predetermine its crystalline properties.

In the context of this invention "contacting/mixing" is understood as placing the at least 2 substances (polyamide and acid) in physical contact, e.g. in a common container, optionally mixing them to increase the amount of areas in contact between the substances.

In the context of this invention "alkyl ester" of the at least mono-substituted α,ω-di-carboxylic acid is understood as an ester between the acid function on one end of the acid and a $C_{1-6}$-alkyl group.

Generally "at least monsubstituted" means either "monosubstituted" or "polysubstituted".

An "aryl", "aryl radical" or group is understood as meaning ring systems with at least one aromatic ring but without heteroatoms even in only one of the rings. Examples are phenyl, naphthyl, fluoranthenyl, fluorenyl, tetralinyl or indanyl, in particular 9H-fluorenyl or anthracenyl radicals, which can be unsubstituted or monosubstituted or polysubstituted.

In the context of this invention "cycloalkyl radical" or group is understood as meaning saturated and unsaturated (but not aromatic) cyclic hydrocarbons (without a heteroatom in the ring), which can be unsubstituted or mono- or polysubstituted. Furthermore, $C_{3-4}$-cycloalkyl represents $C_3$- or $C_4$-cycloalkyl, $C_{3-5}$-cycloalkyl represents $C_3$-, $C_4$- or $C_5$-cycloalkyl, $C_{3-6}$-cycloalkyl represents $C_3$-, $C_4$-, $C_5$- or $C_6$-cycloalkyl, $C_{3-7}$-cycloalkyl represents $C_3$-, $C_4$-, $C_5$-, $C_6$- or $C_7$-cycloalkyl, $C_{3-8}$-cycloalkyl represents $C_3$-, $C_4$-, $C_5$-, $C_6$-, $C_7$- or $C_8$-cycloalkyl, $C_{4-5}$-cycloalkyl represents $C_4$- or $C_5$-cycloalkyl, $C_{4-6}$-cycloalkyl represents $C_4$-, $C_5$- or $C_6$-cycloalkyl, $C_{4-7}$-cycloalkyl represents $C_4$-, $C_5$-, $C_6$- or $C_7$-cycloalkyl, $C_{4-8}$-cycloalkyl represents $C_4$-, $C_5$-, $C_6$- $C_7$ or $C_8$-cycloalkyl $C_{5-6}$-cycloalkyl represents $C_5$- or $C_6$-cycloalkyl and $C_{5-7}$-cycloalkyl represents $C_5$-, $C_6$- or $C_7$-cycloalkyl. However, mono- or polyunsaturated, preferably monounsaturated, cycloalkyls also in particular fall under the term cycloalkyl as long as the cycloalkyl is not an aromatic system. The cycloalkyl radicals are preferably cyclopropyl, 2-methylcyclopropyl, cyclopropylmethyl, cyclobutyl, cyclopentyl, cyclopentylmethyl, cyclohexyl, cycloheptyl, cyclooctyl, and also adamantly.

A "heterocyclyl", a "heterocyclyl radical" or group or "heterocyclic ring system" is understood as meaning heterocyclic ring systems which contain one or more heteroatoms from the group consisting of nitrogen, oxygen and/or sulfur in the ring or ringsystem, and can also be mono- or polysubstituted. The ringsystem may consist either of only one saturated or unsaturated or even aromatic ring or may consist of 2, 3 or 4 saturated or unsaturated or even aromatic rings, which are condensed in that between two or more of the rings ring members are shared. Examples which may be mentioned from the group of heterocyclyls are furan, benzofuran, thiophene, benzothiophene, pyrrole, pyridine, pyrimidine, pyrazine, quinoline, isoquinoline, phthalazine, benzo-1,2,5-thiadiazole, imidazo-thiazole, benzothiazole, indole, benzotriazole, benzodioxolane, benzodioxane, carbazole and quinazoline.

In connection with aryl radical, cycloalkyl radical, or heterocyclyl radical, "substituted" is understood—unless defined otherwise—as meaning replacement of at least one hydrogen radical on the ring-system of the aryl radical, the cycloalkyl radical, or the heterocyclyl radical by OH, SH, =O, halogen (F, Cl, Br, I), CN, $NO_2$, COOH; $NR_xR_y$, with $R_x$ and $R_y$ independently being either H or a saturated or unsaturated, linear or branched, substituted or unsubstituted $C_{1-6}$-alkyl; by a saturated or unsaturated, linear or branched, substituted or unsubstituted $C_{1-6}$-alkyl; a saturated or unsaturated, linear or branched, substituted or unsubstituted —O—$C_{1-6}$-alkyl (alkoxy); a saturated or unsaturated, linear or branched, substituted or unsubstituted —S—$C_{1-6}$-alkyl; a saturated or unsaturated, linear or branched, substituted or unsubstituted —C(O)—$C_{1-6}$-alkyl; a saturated or unsaturated, linear or branched, substituted or unsubstituted —C(O)—O—$C_{1-6}$-alkyl; a substituted or unsubstituted phenyl. "Optionally at least monsubstituted" means either "not substituted" if the option is not fulfilled, "monosubstituted" or "polysubstituted", and "at least monsubstituted" means either "monosubstituted" or "polysubstituted".

Aliphatic radicals/groups, as referred to in the present invention, are optionally mono- or polysubstituted and may be branched or unbranched, saturated or unsaturated. Aliphatic radicals, as defined in the present invention, include alkyl, alkenyl and alkinyl radicals. Unsaturated aliphatic radicals, as defined in the present invention, include alkenyl and alkinyl radicals. Preferred aliphatic radicals according to the present invention include but are not restricted to methyl, ethyl, vinyl (ethenyl), ethinyl, propyl, n-propyl, isopropyl, allyl (2-propenyl), 1-propinyl, methylethyl, butyl, n-butyl, iso-butyl, sec-butyl, tert-butyl butenyl, butinyl, 1-methylpropyl, 2-methylpropyl, 1,1-dimethylethyl, pentyl, n-pentyl, 1,1-dimethylpropyl, 1,2-dimethylpropyl, 2,2-dimethylpropyl, hexyl, 1-methylpentyl, n-heptyl, n-octyl, n-nonyl and n-decyl.

In the context of this invention, alkyl radical or group is understood as meaning saturated and unsaturated, linear or branched hydrocarbons, which can be unsubstituted or mono- or polysubstituted. Thus unsaturated alkyl is understood to encompass alkenyl and alkinyl groups, like e.g. —CH=CH—CH$_3$ or —C≡C—CH$_3$, while saturated alkyl encompasses e.g. —CH$_3$ and —CH$_2$—CH$_3$. In these radicals, $C_{1-2}$-alkyl represents $C_1$- or $C_2$-alkyl, $C_{1-3}$-alkyl represents $C_1$-, $C_2$- or $C_3$-alkyl, $C_{1-4}$-alkyl represents $C_1$-, $C_2$-, $C_3$- or $C_4$-alkyl, $C_{1-5}$-alkyl represents $C_1$-, $C_2$-, $C_3$-, $C_4$-, or $C_5$-alkyl, $C_{1-6}$-alkyl represents $C_1$-, $C_2$-, $C_3$-, $C_4$-, $C_5$- or $C_6$-alkyl, $C_{1-7}$-alkyl represents $C_1$-, $C_2$-, $C_3$-, $C_4$-, $C_5$-, $C_6$- or $C_7$-alkyl, $C_{1-8}$-alkyl represents $C_1$-, $C_2$-, $C_3$-, $C_4$-, $C_5$-, $C_6$-, $C_7$- or $C_8$-alkyl, $C_{1-10}$-alkyl represents $C_1$-, $C_2$-, $C_3$-, $C_4$-, $C_5$-, $C_6$-, $C_7$-, $C_8$-, $C_9$- or $C_{10}$-alkyl and $C_{1-18}$-alkyl represents $C_1$-, $C_2$-, $C_3$-, $C_4$-, $C_5$-, $C_6$-, $C_7$-, $C_8$-, $C_9$-, $C_{10}$-, $C_{11}$-, $C_{12}$-, $C_{13}$-, $C_{14}$-, $C_{15}$-, $C_{16}$-, $C_{17}$- or $C_{18}$-alkyl. The alkyl radicals are preferably methyl, ethyl, vinyl (ethenyl), propyl, allyl (2-propenyl), 1-propinyl, methylethyl, butyl, 1-methylpropyl, 2-methyl-propyl, 1,1-dimethylethyl, pentyl, 1,1-dimethylpropyl, 1,2-dimethylpropyl, 2,2-dimethylpropyl, hexyl, 1-methylpentyl, if substituted also $CHF_2$, $CF_3$ or $CH_2OH$ etc.

In connection with alkylene, alkyl or aliphatic radical or group—unless defined otherwise—the term "substituted" in the context of this invention is understood as meaning replacement of at least one hydrogen radical by F, Cl, Br, I, $NH_2$, SH or OH; within that "monosubstituted" means the substitution of exactly one hydrogen radical, whereas "polysubstituted" means the substitution of more than one hydrogen radical with "polysubstituted" radicals being understood as meaning that the replacement takes effect both on different and on the same atoms several times with the same or different substituents, for example three times on the same C atom, as in the case of $CF_3$, or at different places, as in the case of e.g. —CH(OH)—CH=CH—CHCl$_2$. Therefore, "optionally at least monsubstituted" means either "not substituted" if the option is not fulfilled, "monosubstituted" or "polysubstituted", and "at least monsubstituted" means either "monosubstituted" or "polysubstituted". This definition of "substituted" or the selected substituents generally also applies to the "at least mono-substituted α,ω-di-carboxylic acid or its alkyl ester" or an acid of formula I.

The term "alkylene" is understood as meaning a divalent alkyl group like —CH$_2$— or —CH$_2$—CH$_2$—, with (CH$_2$)$_{3-6}$ being understood as meaning —CH$_2$—CH$_2$—CH$_2$—, —CH$_2$—CH$_2$—CH$_2$—CH$_2$—, —CH$_2$—CH$_2$—CH$_2$—CH$_2$—CH$_2$— and —CH$_2$—CH$_2$—CH$_2$—CH$_2$—CH$_2$—CH$_2$—, (CH$_2$)$_{1-4}$ is to be understood as meaning —CH$_2$—, —CH$_2$—CH$_2$—, —CH$_2$—CH$_2$—CH$_2$— and —CH$_2$—CH$_2$—CH$_2$—CH$_2$—, (CH$_2$)$_{4-5}$ is to be understood as meaning —CH$_2$—CH$_2$—CH$_2$—CH$_2$— and —CH$_2$—CH$_2$—CH$_2$—CH$_2$—CH$_2$—, etc.

In a preferred embodiment of the medical device according to the invention in the production of the polymer the at least mono-substituted di-carboxylic acid is selected from at least mono-substituted oxalic acid, malonic acid, succinic acid, fumaric acid, glutaric acid, adipic acid, 1,7-heptane-dicarboxylic acid, 1,8-octane-di-carboxylic acid, 1,9-nonane-di-carboxylic acid, 1,10-decane-di-carboxylic acid, 1,11-undecane-di-carboxylic acid, 1,12-dodecane-di-carboxylic acid; preferably from adipic acid or 1,10-decane-di-carboxylic acid.

In another preferred embodiment of the medical device according to the invention in the production of the polymer the at least mono-substituted di-carboxylic acid is a compound of general formula I $$HOOC-(CH_2)_m-CHR^1-(CH_2)_n-COOR^2$$

wherein
m and n are independently from each other selected from a natural number and 0 and n+m is between 1 and 9, preferably between 3 and 7;
$R^2$ is selected from hydrogen or $C_{1-4}$-alkyl;
$R^1$ is any radical, preferably a sterically voluminous group.

In the context of this invention a "sterically voluminous group" is understood as a radical that due to its steric effect, derived from the amount of space occupied by atoms of the molecule, does give a relatively high effect of steric hindrance. Steric effects arise from the fact that each atom within a molecule occupies a certain amount of space. If atoms are brought too close together, there is an associated cost in energy, and this may affect the molecule's preferred shape and chemical reaction. Steric hindrance occurs when the size of groups within a molecule prevents chemical reactions that are observed in related smaller molecules or may also restrict molecular geometry between adjacent groups.

In another preferred embodiment of the medical device according to the invention in the production of the polymer according to formula I
either
m and n are independently from each other selected from 0, 1, 2 or 3 and n+m is 3;
or
m and n are independently from each other selected from 0, 1, 2, 3, 4, 5, 6 or 7 and n+m is 7;
preferably wherein
m and n are independently from each other selected from 0, 1, 2 or 3 and n+m is 3.

In another preferred embodiment of the medical device according to the invention in the production of the polymer the at least mono-substituted di-carboxylic acid is a compound of general formula II wherein
one of $R^{3'}$ and $R^3$ is selected from hydrogen, while the other may be either hydrogen or $C_{1-4}$-Alkyl;
0, 1 or 2 of the bonds marked by a dotted line ----- may be a double bond, with the proviso, that if there are 2 double bonds they may not touch the same C-atom;
$R^1$ is any radical, preferably a sterically voluminous group.

In another preferred embodiment of the medical device according to the invention in the production of the polymer in the at least mono-substituted di-carboxylic acid according to either formula I or II
$R^1$ is selected from halogen; a branched or linear, saturated or non-saturated, optionally substituted $C_{1-6}$ aliphatic radical; an optionally substituted Aryl; a saturated or non-saturated, optionally substituted $C_{3-10}$-Cycloalkyl; an optionally substituted heterocyclyl.

In another preferred embodiment of the medical device according to the invention in the production of the polymer the at least mono-substituted α-ω-di-carboxylic acid is 3-tert. butyl adipic acid.

In another preferred embodiment of the medical device according to the invention in the production of the polymer the polyamide is a structure of general formula III or IIIa

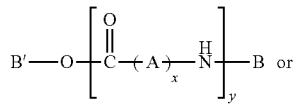

(III)

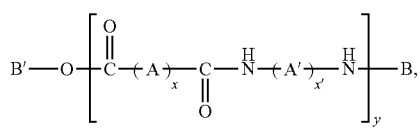

(IIIa)

preferably a structure of general formula III,
wherein
A is a divalent, branched or linear, saturated or non-saturated, optionally substituted hydrocarbon chain, with optionally at least one carbon atom being replaced by a heteroatom selected from N, O or S;
A' is a divalent, branched or linear, saturated or non-saturated, optionally substituted hydrocarbon chain, with optionally at least one carbon atom being replaced by a heteroatom selected from N, O or S;
B and B' independently from one another are selected from H or $C_{1-4}$-Alkyl;
x is a natural number between 1 and 24;
x' is a natural number between 1 and 24;
y is a natural number $\geq 1$ In another preferred embodiment of the medical device according to the invention in the production of the polymer in the structure according to general formula III or IIIa
A is a branched or linear, saturated or non-saturated, optionally substituted divalent aliphatic group; preferably is optionally substituted alkylene; more preferably is —$CH_2$—;
A' is a branched or linear, saturated or non-saturated, optionally substituted divalent aliphatic group; preferably is optionally substituted alkylene; more preferably is —$CH_2$—;
and/or
x is a natural number between 3 and 13, preferably is a natural number between 5 and 11; more preferably is 5, 10 or 11, most preferably is 11 or 5;
x' is a natural number between 3 and 13, preferably is a natural number between 5 and 11; more preferably is 5, 10 or 11, most preferably is 11 or 5;
preferably,
if the polyamide is a structure according to general formula III,
A is a branched or linear, saturated or non-saturated, optionally substituted divalent aliphatic group; preferably is optionally substituted alkylene; more preferably is —$CH_2$—;
and/or
x is a natural number between 3 and 13, preferably is a natural number between 5 and 11; more preferably is 5, 10 or 11, most preferably is 11.

In another preferred embodiment of the medical device according to the invention in the production of the polymer the polyamide is selected from Nylon 6; Nylon 6,6; Nylon 11; or Nylon 12; preferably is Nylon 12.

In another preferred embodiment of the medical device according to the invention in the production of the polymer the polyamide is selected from Nylon 6; Nylon 6,6; Nylon 11; or Nylon 12; preferably is Nylon 12
and
the at least mono-substituted α,ω-di-carboxyloc acid is 3-tert. butyl adipic acid.

In another preferred embodiment of the medical device according to the invention in the production of the polymer the at least mono-substituted α,ω-di-carboxylic acid is added in an amount resulting in a molar ratio between the acid and the polyamide (wherein the molarity of the polyamide is calculated relatively based on the equivalent number of theoretical lactam units in the polyamide) of between 0.05 and 0.0005, preferably between 0.025 and 0.001.

In another preferred embodiment of the medical device according to the invention in the production of the polymer the at least mono-substituted α,ω-di-carboxylic acid is added in an amount resulting in a molar ratio between the acid and the polyamide calculated (wherein the molarity of the polyamide is calculated relatively based on the number and molecular weight of the polymerized amide building block

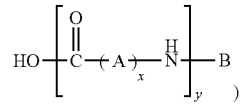

and the molar ratio results in between 0.05 and 0.0005, preferably between 0.025 and 0.001.

Thus, e.g. if mixing Y grams of di-carboxylic acid and X grams of polyamide, the amount of acid is divided by its molecular weight to give the molarity, while the amount of polyamide is divided by the molecular weight of the building block/the theoretical basic lactam unit to give its relative molarity. Then the relative molecular ratio of acid:polyamide is calculated.

In another preferred embodiment of the medical device according to the invention in the production of the polymer the reaction is executed using reactive extrusion.

Another aspect of the invention refers to a medical device B comprising a polymer (named polymer B hereafter) according to general formula IV or IVa

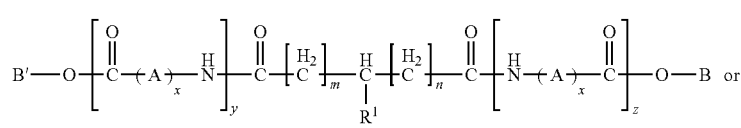

(IV)

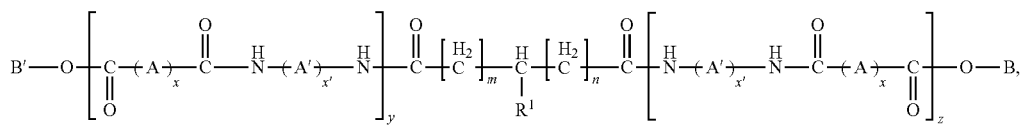

(Iva)

preferably IV,
wherein
A is a divalent, branched or linear, saturated or non-saturated, optionally substituted hydrocarbon chain, with optionally at least one carbon atom being replaced by a heteroatom selected from N, O or S;
A' is a divalent, branched or linear, saturated or non-saturated, optionally substituted hydrocarbon chain, with optionally at least one carbon atom being replaced by a heteroatom selected from N, O or S;
B and B' independently from one another are selected from H or $C_{1-4}$-Alkyl;
x is a natural number between 1 and 24;
x' is a natural number between 1 and 24;
y is a natural number $\geq 1$.
z is a natural number $\geq 1$ or 0;
m and n are independently from each other selected from 0 and a natural number between 1 and 9 and n+m is a natural number between 1 and 9; and
$R^1$ is any radical, preferably a sterically voluminous group.

In another preferred embodiment of the medical device B according to the invention for polymer B it applies that y+z$\geq$10.

In another preferred embodiment of the medical device B according to the invention for polymer B it applies that the polymer is of general formula V

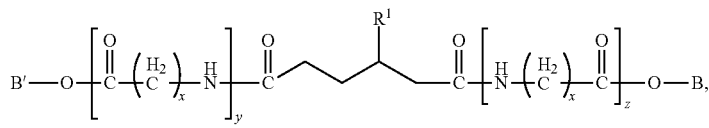

wherein
B and B' independently from one another are selected from H or $C_{1-4}$-Alkyl;
x is a natural number between 1 and 24;
y is a natural number $\geq 1$.
z is a natural number $\geq 1$ or 0;
$R^1$ is selected from halogen; a branched or linear, saturated or non-saturated, optionally substituted $C_{1-6}$ aliphatic radical; an optionally substituted Aryl; a saturated or non-saturated, optionally substituted $C_{3-10}$-Cycloalkyl; an optionally substituted heterocyclyl.

In a preferred embodiment of the medical device B according to the invention for polymer B it applies that y+z$\geq$10.

In another preferred embodiment of the medical device B according to the invention for polymer B according to formula IV, IVa and/or V
B and B' are hydrogen;
and/or
x is a natural number between 3 and 13, preferably is a natural number between 5 and 11; preferably is 5, 10 or 11, more preferably is 5 or 11, most preferably is 11;
and/or
z is 0;
and/or
z+y is between 20 and 2000, preferably 40 and 1000;
and/or
$R^1$ is selected from halogen; a branched or linear, saturated or non-saturated, optionally substituted $C_{1-4}$ alkyl-radical, preferably is iso-propyl or tert. butyl, more preferably is tert. butyl.

Most preferably here in another preferred embodiment of the medical device B according to the invention for polymer B according to formula IV, IVa and/or V
x is 11;
and
$R^1$ is tert. butyl.

In another preferred embodiment of the medical device or medical device B according to the invention the polymer or the polymer B is modified in at least one of the end groups with liquid crystalline oligomers (LCOs/LC-oligomers).

In a very preferred embodiment the medical device or the medical device B according to the invention is selected from implanted or implantable medical devices, more preferably is selected from (medical) balloons or balloon material, stents, stent grafts, grafts, graft connectors or catheters.

"Balloon", "Medical Balloon" or "balloon material" in the context of this invention especially means a balloon like those used in (coronary) balloon angioplasty (PTA/PTCA) and the material used for these balloons, especially balloon catheters.

In this, e.g. a balloon catheter is inserted into an artery or other lumen and advanced to e.g. a narrowing in a coronary artery. The balloon is then inflated by gas or fluids to enlarge the lumen and/or—often—to place a medical device.

"Stent" means an elongate implant with a hollow interior and at least two orifices and usually a circular or elliptical, but also any other, cross section, preferably with a perforated, lattice-like structure that is implanted into vessels, in particular blood vessels, to restore and maintain the vessels patent and functional.

"Graft" means an elongate implant with a hollow interior and with at least two orifices and usually circular or elliptical, but also any other, a cross section and with at least one closed polymer surface which is homogeneous or, optionally, woven from various strands. The surface preferably is impermeable to corpuscular constituents of blood and/or for water, so that the implant serves as a vascular prosthesis and is usually employed for damaged vessels or in place of vessels.

"Stent graft" means a connection between a stent and a graft. A stent graft preferably comprises a vascular prosthesis reinforced with a stent (both as defined above), wherein a polymer layer is homogeneous or, optionally, woven, knitted plaited etc. from various strands and is either impermeable for corpuscular constituents of blood and/or for water or can also be permeable. More preferably, the stent has on at least 20% of its surface a perforated (lattice-like), preferably metallic, outer layer and at least one closed polymer layer that is located inside or outside the stent outer layer. The closed polymer layer may be homogeneous or, optionally, woven from various strands, and is impermeable for corpuscular constituents of blood and/or for water. Optionally, where the closed polymer layer is disposed inside the metallic outer layer, a further perforated (lattice-like), preferably metallic, inner layer may be located inside the polymer layer.

"Graft connector" means an implant that connects at least two hollow organs, vessels or grafts, consists of the materials defined for grafts or stent grafts and/or has the structure defined for the latter. Preferably, a graft connector has at least two, three or four, orifices, arranged, for example, as an asymmetric "T" shape.

"Catheter" means a tubular instrument intended for introduction into hollow organs. More preferably, a catheter may be designed for use in guiding other catheters, or for angiography, ultrasound imaging, or—especially—balloon catheters for dilatation or stent delivery. This includes also a "Catheter pump" meaning a catheter provided on its tip with a propeller able to assist the pumping of the myocardium.

In a further aspect the invention resides in a polymer producible by contacting/mixing one or more polyamides with an at least mono-substituted α,ω-di-carboxylic acid or its alkyl ester and heating to a temperature above 150° C.

In an embodiment of the polymer the proviso applies that the at least mono-substituted α,ω-di-carboxylic acid may not be methyl adipic acid, preferably may not be 3-methyl adipic acid.

In a preferred embodiment the heating is done
a) already during the mixing/contacting and/or
b) under protective gas atmosphere, preferably under argon and/or
c) to a temperature above 200° C., preferably above 220° C. and/or
d) in 2 steps with different temperatures preferably divided by an intermediate step in which the second temperature is reached within a certain time limit and/or
e) over a time period of more than 3 h, preferably of more than 4 h.

Most preferably the mixing is done under protective gas atmosphere—preferably under argon—in a first heating step at more than 200° C.—preferably 220° C.—for more than 1 h—preferably 2 h. The temperature was consequently raised within 10 to 30 min—preferably within 20 min—to more than 220° C.—preferably to 250° C.—and the mixture was stirred for another 2 h.

In a preferred embodiment of the polymer according to the invention the at least mono-substituted di-carboxylic acid is selected from at least mono-substituted oxalic acid, malonic acid, succinic acid, fumaric acid, glutaric acid, adipic acid, 1,7-heptane-dicarboxylic acid, 1,8-octane-di-carboxylic acid, 1,9-nonane-di-carboxylic acid, 1,10-decane-di-carboxylic acid, 1,11-undecane-di-carboxylic acid, 1,12-dodecane-di-carboxylic acid; preferably from adipic acid or 1,10-decane-di-carboxylic acid.

In another preferred embodiment of the polymer according to the invention the at least mono-substituted di-carboxylic acid is a compound of general formula I

wherein
m and n are independently from each other selected from a natural number and 0 and n+m is between 1 and 9, preferably between 3 and 7;
$R^2$ is selected from hydrogen or $C_{1-4}$-alkyl;
$R^1$ is any radical, preferably a sterically voluminous group.

In another preferred embodiment of the polymer according to the invention according to formula I
either
m and n are independently from each other selected from 0, 1, 2 or 3 and n+m is 3;
or
m and n are independently from each other selected from 0, 1, 2, 3, 4, 5, 6 or 7 and n+m is 7;
preferably wherein
m and n are independently from each other selected from 0, 1, 2 or 3 and n+m is 3.

In another preferred embodiment of the polymer according to the invention the at least mono-substituted di-carboxylic acid is a compound of general formula II

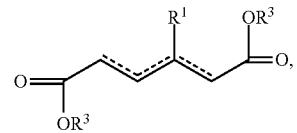

wherein
one of $R^{3'}$ and $R^3$ is selected from hydrogen, while the other may be either hydrogen or $C_{1-4}$-Alkyl;
0, 1 or 2 of the bonds marked by a dotted line ---- may be a double bond, with the proviso, that if there are 2 double bonds they may not touch the same C-atom;
$R^1$ is any radical, preferably a sterically voluminous group.

In another preferred embodiment of the polymer according to the invention according to either formula I or II
$R^1$ is selected from halogen; a branched or linear, saturated or non-saturated, optionally substituted $C_1$ aliphatic radical; an optionally substituted Aryl; a saturated or non-saturated, optionally substituted $C_{3-10}$-Cycloalkyl; an optionally substituted heterocyclyl.

In another preferred embodiment of the polymer according to the invention the at least mono-substituted α-ω-di-carboxylic acid is 3-tert. butyl adipic acid.

In another preferred embodiment of the polymer according to the invention the polyamide is a structure of general formula III or IIIa

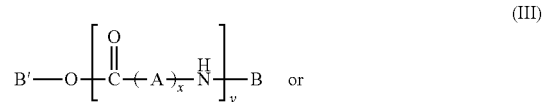

(III)

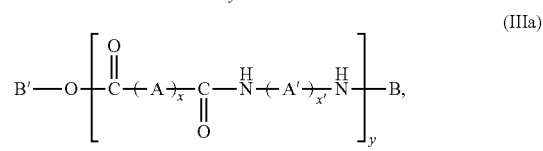

(IIIa)

preferably a structure of general formula III,
wherein
A is a divalent, branched or linear, saturated or non-saturated, optionally substituted hydrocarbon chain, with optionally at least one carbon atom being replaced by a heteroatom selected from N, O or S;

A' is a divalent, branched or linear, saturated or non-saturated, optionally substituted hydrocarbon chain, with optionally at least one carbon atom being replaced by a heteroatom selected from N, O or S;

B and B' independently from one another are selected from H or $C_{1-4}$-Alkyl;

x is a natural number between 1 and 24;

x' is a natural number between 1 and 24;

y is a natural number $\geq 1$.

In another preferred embodiment of the polymer according to the invention in the structure according to general formula III or IIIa A is a branched or linear, saturated or non-saturated, optionally substituted divalent aliphatic group; preferably is optionally substituted alkylene; more preferably is —$CH_2$—;

A' is a branched or linear, saturated or non-saturated, optionally substituted divalent aliphatic group; preferably is optionally substituted alkylene; more preferably is —$CH_2$—;

and/or x is a natural number between 3 and 13, preferably is a natural number between 5 and 11; more preferably is 5, 10 or 11, most preferably is 11 or 5;

x' is a natural number between 3 and 13, preferably is a natural number between 5 and 11; more preferably is 5, 10 or 11, most preferably is 11 or 5;

preferably, if the polyamide is a structure according to general formula III,

A is a branched or linear, saturated or non-saturated, optionally substituted divalent aliphatic group; preferably is optionally substituted alkylene; more preferably is —$CH_2$—;

and/or x is a natural number between 3 and 13, preferably is a natural number between 5 and 11; more preferably is 5, 10 or 11, most preferably is 11.

In another preferred embodiment of the polymer according to the invention the polyamide is selected from Nylon 6; Nylon 6,6; Nylon 11; or Nylon 12; preferably is Nylon 12.

In another preferred embodiment of the polymer according to the invention the polyamide is selected from Nylon 6; Nylon 6,6; Nylon 11; or Nylon 12; preferably is Nylon 12 and the at least mono-substituted α,ω-di-carboxyloc acid is 3-tert. butyl adipic acid.

In another preferred embodiment of the polymer according to the invention the at least mono-substituted am-di-carboxylic acid is added in an amount resulting in a molar ratio between the acid and the polyamide (wherein the molarity of the polyamide is calculated relatively based on the equivalent number of theoretical lactam units in the polyamide) of between 0.05 and 0.0005, preferably between 0.025 and 0.001.

In another preferred embodiment of the polymer according to the invention the at least mono-substituted α,ω-di-carboxylic acid is added in an amount resulting in a molar ratio between the acid and the polyamide calculated (wherein the molarity of the polyamide is calculated relatively based on the number and molecular weight of the polymerized amide building block

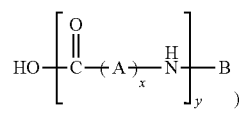

and the molar ratio results in between 0.05 and 0.0005, preferably between 0.025 and 0.001.

Thus, e.g. if mixing Y grams of di-carboxylic acid and X grams of polyamide, the amount of acid is divided by its molecular weight to give the molarity, while the amount of polyamide is divided by the molecular weight of the building block/the theoretical basic lactam unit to give its relative molarity. Then the relative molecular ratio of acid:polyamide is calculated.

In another preferred embodiment of the polymer according to the invention the reaction is executed using reactive extrusion.

Another aspect of the invention refers to a polymer (named polymer B hereafter) according to general formula IV or IVa

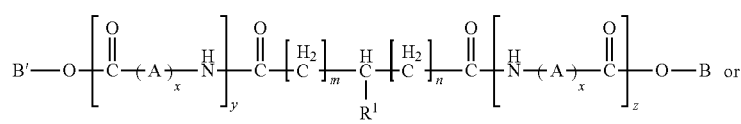

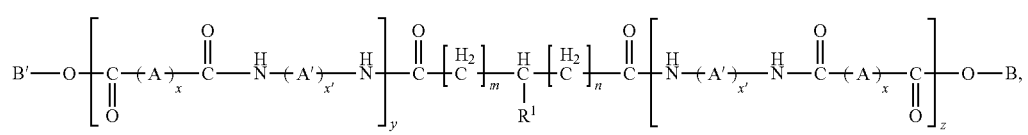

preferably IV, wherein

A is a divalent, branched or linear, saturated or non-saturated, optionally substituted hydrocarbon chain, with optionally at least one carbon atom being replaced by a heteroatom selected from N, O or S;

A' is a divalent, branched or linear, saturated or non-saturated, optionally substituted hydrocarbon chain, with optionally at least one carbon atom being replaced by a heteroatom selected from N, O or S;

B and B' independently from one another are selected from H or $C_{1-4}$-Alkyl;

x is a natural number between 1 and 24;

x' is a natural number between 1 and 24;

y is a natural number $\geq 1$.

z is a natural number $\geq 1$ or 0;

m and n are independently from each other selected from 0 and a natural number between 1 and 9 and n+m is a natural number between 1 and 9; and $R^1$ is any radical, preferably a sterically voluminous group.

In an embodiment of the polymer B according to formula IV or IVa the proviso applies that $R^1$ may not be methyl.

In another preferred embodiment of the polymer B it applies that y+z≧10.

In another preferred embodiment of the polymer B according to the invention the polymer is of general formula V

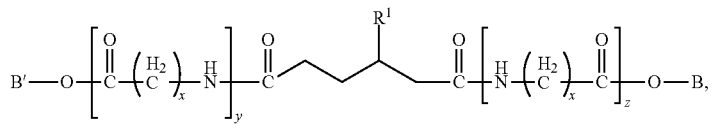

wherein
B and B' independently from one another are selected from H or $C_{1-4}$-Alkyl;
x is a natural number between 1 and 24;
y is a natural number ≧1.
z is a natural number ≧1 or 0;
$R^1$ is selected from halogen; a branched or linear, saturated or non-saturated, optionally substituted $C_{1-6}$ aliphatic radical; an optionally substituted Aryl; a saturated or non-saturated, optionally substituted $C_{3-10}$-Cycloalkyl; an optionally substituted heterocyclyl.

In an embodiment of the polymer B according to formula V the proviso applies that $R^1$ may not be methyl.

In a preferred embodiment of the polymer B it applies that y+z≧10.

In another preferred embodiment of the polymer B according to the invention according to formula IV, IVa and/or V
B and B' are hydrogen;
and/or
x is a natural number between 3 and 13, preferably is a natural number between 5 and 11; preferably is 5, 10 or 11, more preferably is 5 or 11, most preferably is 11;
and/or
z is 0;
and/or
z+y is between 20 and 2000, preferably 40 and 1000;
and/or
$R^1$ is selected from halogen; a branched or linear, saturated or non-saturated, optionally substituted $C_{1-4}$ alkyl-radical, preferably is iso-propyl or tert. butyl, more preferably is tert. butyl.

Most preferably in another preferred embodiment of the polymer B according to the invention according to formula IV, IVa and/or V
x is 11;
and
$R^1$ is tert. butyl.

In another preferred embodiment of the polymer B or the polymer according to the invention the polymer is modified in at least one of the end groups with liquid crystalline oligomers (LCOs/LC-oligomers).

Another aspect of the invention provides a process for the production of a polymer B according to the invention, wherein one or more polyamide/s is contacted/mixed with an at least mono-substituted α,ω-di-carboylic acid, preferably at least mono-substituted adipic acid, and then the mixture is heated to a temperature above 150° C.

In another preferred embodiment of the process for polymer B according to the invention the at least mono-substituted α,ω-di-carboylic acid, preferably the at least mono-substituted adipic acid is added in an amount resulting in a molar ratio between the acid and the polyamide calculated relatively based on the equivalent number of lactam Units in the polyamide between 0.05 and 0.0005, preferably between 0.025 and 0.001;

or in an amount resulting in a molar ratio between the acid and the polyamide calculated relatively based on molecular weight of the polymerized amide building block

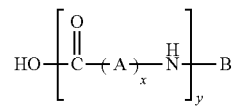

between 0.05 and 0.0005, preferably between 0.025 and 0.001.

In another preferred embodiment of the process for polymer B according to the invention the reaction is executed using reactive extrusion.

Another aspect of the current invention provides the use of a polymer, including polymer B, according to the invention in the production of implants or medical devices, preferably implanted or implantable medical devices, more preferably for the production of balloon/balloon material, of stents, stent grafts, grafts graft connectors or catheters.

In a further embodiment the invention is directed to a method of treatment of a disease, like a cardiovascular disease, especially a stenosis, using in a patient, being a mammal, especially a human, in need thereof a medical device or medical device B according to the invention, desirably in minimal invasive surgery like PTA or PTCA.

In yet another embodiment the invention is directed to the use of a medical device or medical device B according to the invention for the treatment of a disease, like a cardiovascular disease, especially a stenosis, especially through minimal invasive surgery like PTA or PTCA.

The examples and figures in the following section describing the use of the polyamides are merely illustrative and the invention cannot be considered in any way as being restricted to these applications.

EXAMPLES

Example 1

(1.4%; Normal Reaction)

50 g dried Nylon 12 (with a molecular weight of approx. 26000 g/mol) was mixed with 0.688 g (0.0034 mol) 3-tert. butyl adipic acid under argon for 2 h at 220° C. The temperature was raised within 20 min to 250° C. and the mixture was stirred for another 2 h. The resulting solid gave a molecular weight of 13000 g/mol. The relative molar ratio (see above) was 0.013, being calculated as 0.0034 mol (acid): 0.253 rel. mol (Polyamid: MW (building block) 197.3).

Example 2

(1.4%; Extrusion)

The reaction of example 1 is carried out in an extruder by way of the so-called (reactive extrusion) as described in DD 276 290 A1 and Eichhorn et al. (Journal of Applied Polymer Science, Vol. 62, 2053-2060 (1996). Reaction time in each of the 2 steps is reduced to below 30 min.

Example 3

(0.5%; Normal Reaction)

1651 g dried Nylon 12 (with a molecular weight of approx. 26000 g/mol) is mixed with 8.25 g (0.040 mol) 3-tert. butyl adipic acid under argon for 2 h at 220° C. The temperature is raised within 20 min to 250° C. and the mixture is stirred for another 2 h. The relative molar ratio (see above) is 0.0048, being calculated as 0.040 mol (acid): 8.368 rel. mol (Polyamid: MW (building block) 197.3).

Example 4

(0.25%; Normal Reaction)

1753 g dried Nylon 12 (with a molecular weight of approx. 26000 g/mol) is mixed with 4.38 g (0.022 mol) 3-tert. butyl adipic acid under argon for 2 h at 220° C. The temperature is raised within 20 min to 250° C. and the mixture is stirred for another 2 h. The relative molar ratio (see above) is 0.0025, being calculated as 0.022 mol (acid): 8.885 rel. mol (Polyamid: MW (building block) 197.3).

Example 5

(2.0%; Normal Reaction)

1694 g dried Nylon 12 (with a molecular weight of approx. 26000 g/mol) is mixed with 33.88 g (0.167 mol) 3-tert. butyl adipic acid under argon for 2 h at 220° C. The temperature is raised within 20 min to 250° C. and the mixture is stirred for another 2 h. The relative molar ratio (see above) is 0.0195, being calculated as 0.167 mol (acid): 8.586 rel. mol (Polyamid: MW (building block) 197.3).

Example 6

(Comparative Example)

Same as example 1 with the exception that instead of 0.0034 mol 3-tert. butyl adipic acid 0.0034 mol non-substituted adipic acid is added.

Test of Mechanical Properties:

The material according to example 1 was compared to the unmodified Nylon 12 and showed better flexibility than the Nylon and seems to show—calculated based on comparison to literature standards—a higher rigidity than PEBAX®

Example 6 yielded a brittle polymer with very poor mechanical properties, which was due to that fact not testable by the methods shown above.

The invention claimed is:

1. Medical device comprising a polymer produced by (i) contacting/mixing one or more polyamides with an at least mono-substituted α,ω-di-carboxylic acid or an alkyl ester of the at least mono-substituted α,ω-di-carboxylic acid and (ii) heating to a temperature above 150° C.

2. Medical device according to claim 1, where the at least mono-substituted di-carboxylic acid is selected from the group consisting of an at least mono-substituted oxalic acid (2), malonic acid (3), succinic acid (4), fumaric acid (4), glutaric acid (5), adipic acid, 1,7-heptane-dicarboxylic acid, 1,8-octane-di-carboxylic acid, 1,9-nonane-di-carboxylic acid, 1,10-decane-di-carboxylic acid, 1,11-undecane-di-carboxylic acid, and 1,12-dodecane-di-carboxylic acid.

3. Medical device according to claim 1, wherein the at least mono-substituted di-carboxylic acid is a compound of formula I

wherein m and n are independently from each other selected from the group consisting of a natural number and 0 and n+m is a number between 1 and 9;

$R^2$ and $R^{2'}$ are independently from each other selected from the group consisting of OH, halogen and O—$C_{1-4}$-alkyl;

$R^1$ is any radical except hydrogen.

4. Medical device according to claim 3, wherein either m and n are independently from each other are selected from 0, 1, 2 or 3 and n+m is 3;

or m and n are independently from each other selected from 0, 1, 2, 3, 4, 5, 6 or 7 and n+m is 7.

5. Medical device according to claim 1, wherein the at least mono-substituted di-carboxylic acid is a compound of formula II

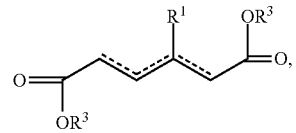

wherein one of $R^{3'}$ and $R^3$ is selected from hydrogen, while the other may be either hydrogen or $C_{1-4}$-alkyl;

0, 1 or 2 of the bonds marked by a dotted line ⋯ may be a double bond, with the proviso, that if there are 2 double bonds they may not touch the same C-atom; and $R^1$ is any radical except hydrogen.

6. Medical device according to claim 5, wherein $R^1$ is selected from the group consisting of halogen; a branched or linear, saturated or non-saturated, optionally substituted $C_{1-6}$ aliphatic radical; an optionally substituted aryl; a saturated or non-saturated, optionally substituted $C_{3-10}$-Cycloalkyl; and an optionally substituted heterocyclyl.

7. Medical device according to claim 1, wherein the at least mono-substituted di-carboxylic acid is 3-tert. butyl adipic acid.

8. Medical device according to claim 1, wherein the polyamide is a structure of formula III or IIIa

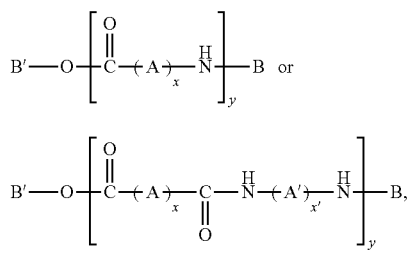

wherein
A is a divalent, branched or linear, saturated or non-saturated hydrocarbon chain, wherein optionally at least one hydrogen radical of the divalent, branched or linear, saturated or non-saturated hydrocarbon chain is replaced by F, Cl, Br, I, $NH_2$, SH or OH, with optionally one carbon atom of the divalent, branched or linear, saturated or non-saturated hydrocarbon chain being replaced by NH, O or S;

A' is a divalent, branched or linear, saturated or non-saturated hydrocarbon chain, wherein optionally at least one hydrogen radical of the divalent, branched or linear, saturated or non-saturated hydrocarbon chain is replaced by F, Cl, Br, I, $NH_2$, SH or OH, with optionally one carbon atom of the divalent, branched or linear, saturated or non-saturated hydrocarbon chain being replaced by NH, O or S;

B and B' independently from one another are selected from H or $C_{1-4}$-Alkyl;

x is a natural number between 1 and 24;

x' is a natural number between 1 and 24; and y of Formula III is a natural number >1 and y of Formula IIIa is a natural number ≧1.

9. Medical device according to claim 8, wherein
A is a branched or linear, saturated or non-saturated, divalent aliphatic group, wherein at least one hydrogen radical of the branched or linear, saturated or non-saturated, divalent aliphatic group is optionally replaced by F, Cl, Br, I, $NH_2$, SH or OH;

A' is a branched or linear, saturated or non-saturated, divalent aliphatic group, wherein at least one hydrogen radical of the branched or linear, saturated or non-saturated, divalent aliphatic group is optionally replaced by F, Cl, Br, I, $NH_2$, SH or OH;

and/or x is a natural number between 3 and 13;

x' is a natural number between 3 and 13; or if the polyamide is a structure according to formula III, A is a branched or linear, saturated or non-saturated, divalent aliphatic group, wherein at least one hydrogen radical of the branched or linear, saturated or non-saturated, divalent aliphatic group is optionally replaced by F, Cl, Br, I, $NH_2$, SH or OH;

and/or x is a natural number between 3 and 13.

10. Medical device according to claim 1, wherein the polyamide is selected from the group consisting of Nylon 6; Nylon 6,6; Nylon 11; and Nylon 12;
and
the at least mono-substituted α,ω-di-carboxylic acid is 3-tert. butyl adipic acid.

11. Medical device according to claim 1, wherein the at least mono-substituted α,ω-di-carboxylic acid is added in an amount resulting in a molar ratio between the acid and the polyamide calculated relatively based on the equivalent number of lactam Units in the polyamide between 0.05 and 0.0005.

12. Medical device according to claim 1, wherein the at least mono-substituted α,ω-di-carboxylic acid is added in an amount resulting in a molar ratio between the acid and the polyamide calculated relatively based on molecular weight of the polymerized amide building block

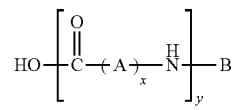

between 0.05 and 0.0005, wherein y is a natural number >1.

13. Medical device according to claim 1, wherein the contacting/mixing and the heating are executed using reactive extrusion.

14. Medical device according to claim 1, wherein the polymer produced by (i) contacting/mixing one or more polyamides with an at least mono-substituted α,ω-di-carboxylic acid or an alkyl ester of the at least mono-substituted α,ω-di-carboxylic acid and (ii) heating to a temperature above 150° C. is modified in at least one of end group with liquid crystalline oligomers (LCOs/LC-oligomers).

15. Medical device according to claim 1, selected from the group consisting of balloon/balloon material, stents, stent grafts, grafts, graft connectors and catheters.

16. Medical device comprising a polymer according to formula IV or IVa

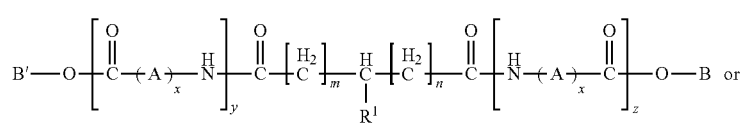

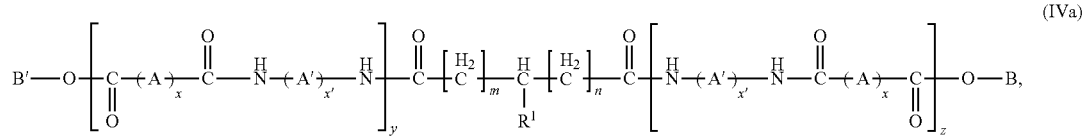

wherein
A is a divalent, branched or linear, saturated or non-saturated hydrocarbon chain, wherein optionally at least one hydrogen radical of the divalent, branched or linear, saturated or non-saturated hydrocarbon chain is replaced by F, Cl, Br, I, $NH_2$, SH or OH, with optionally one carbon atom of the divalent, branched or linear, saturated or non-saturated hydrocarbon chain being replaced by NH, O or S;

A' is a divalent, branched or linear, saturated or non-saturated hydrocarbon chain, wherein optionally at least one hydrogen radical of the divalent, branched or linear, saturated or non-saturated hydrocarbon chain is replaced by F, Cl, Br, I, $NH_2$, SH or OH, with optionally one carbon atom of the divalent, branched or linear, saturated or non-saturated hydrocarbon chain being replaced by NH, O or S;

B and B' independently from one another are selected from H or $C_{1-4}$-Alkyl;

x is a natural number between 1 and 24;
x' is a natural number between 1 and 24;
y is a natural number $\geq 1$;
z is a natural number $\geq 1$ or 0;
m and n are independently from each other selected from 0 and a natural number between 1 and 9 and n+m is a natural number between 1 and 9; and
$R^1$ is any radical.

17. Medical device according to claim 16, wherein the polymer is of formula V

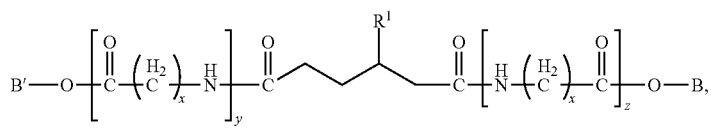

wherein

B and B' independently from one another are selected from H or $C_{1-4}$-alkyl;

x is a natural number between 1 and 24;
y is a natural number $\geq 1$;
z is a natural number $\geq 1$ or 0;
$R^1$ is selected from the group consisting of halogen; a branched or linear, saturated or non-saturated, optionally substituted $C_{1-6}$ aliphatic radical; an optionally substituted aryl; a saturated or non-saturated, optionally substituted $C_{3-10}$-cycloalkyl; and an optionally substituted heterocyclyl.

18. Medical device according to claim 17, wherein
B and B' are hydrogen;
and/or
x is a natural number between 3 and 13;
and/or
z is 0;
and/or
z+y is between 20 and 2000;
and/or
$R^1$ is selected from the group consisting of halogen; and a branched or linear, saturated or non-saturated, optionally substituted $C_{1-4}$ alkyl-radical.

19. Medical device according to claim 17, wherein
x is 11;
and
$R^1$ is tertiary butyl.

20. Polymer produced by (i) contacting/mixing one or more polyamides with an at least mono-substituted α,ω-di-carboxylic acid or an alkyl ester of the at least mono-substituted α,ω-di-carboxylic acid and (ii) heating to a temperature above 150° C.;
with the proviso that the mono-substituted α,ω-di-carboxylic acid is not methyl-adipic acid.

21. Polymer according to claim 20, where the at least mono-substituted di-carboxylic acid is selected from the group consisting of an at least mono-substituted oxalic acid (2), malonic acid (3), succinic acid (4), fumaric acid (4), glutaric acid (5), adipic acid, 1,7-heptane-dicarboxylic acid, 1,8-octane-di-carboxylic acid, 1,9-nonane-di-carboxylic acid, 1,10-decane-di-carboxylic acid, 1,11-undecane-di-carboxylic acid, and 1,12-dodecane-di-carboxylic acid.

22. Polymer according to claim 20, wherein the at least mono-substituted di-carboxylic acid is 3-tert. butyl adipic acid.

23. Polymer according to claim 20, wherein the polyamide is a structure of formula III or IIIa

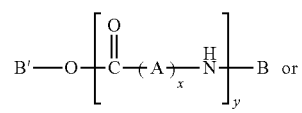

-continued

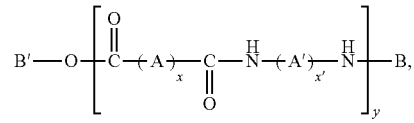

wherein

A is a divalent, branched or linear, saturated or non-saturated hydrocarbon chain, wherein optionally at least one hydrogen radical of the divalent, branched or linear, saturated or non-saturated hydrocarbon chain is replaced by F, Cl, Br, I, $NH_2$, SH or OH, with optionally one carbon atom of the divalent, branched or linear, saturated or non-saturated hydrocarbon chain being replaced by NH, O or S;

A' is a divalent, branched or linear, saturated or non-saturated hydrocarbon chain, wherein optionally at least one hydrogen radical of the divalent, branched or linear, saturated or non-saturated hydrocarbon chain is replaced by F, Cl, Br, I, $NH_2$ SH or OH, with optionally one carbon atom of the divalent, branched or linear, saturated or non-saturated hydrocarbon chain being replaced by NH, O or S;

B and B' independently from one another are selected from H or $C_{1-4}$-Alkyl;

x is a natural number between 1 and 24;
x' is a natural number between 1 and 24;
y of Formula III is a natural number >1 and y of Formula IIIa is a natural number $\geq 1$.

24. Polymer according to claim 20, wherein the polyamide is selected from the group consisting of Nylon 6; Nylon 6,6; Nylon 11; and Nylon 12;
and the at least mono-substituted α,ω-di-carboxylic acid is 3-tert. butyl adipic acid.

25. Polymer according to claim 20, wherein the at least mono-substituted α,ω-di-carboxylic acid is added in an amount resulting in a molar ratio between the acid and the polyamide calculated relatively based on the equivalent number of lactam Units in the polyamide between 0.05 and 0.0005.

26. Polymer according to claim 20, wherein the at least mono-substituted α,ω-di-carboxylic acid is added in an amount resulting in a molar ratio between the acid and the polyamide calculated relatively based on molecular weight of the polymerized amide building block

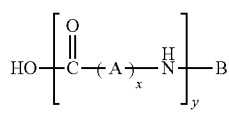

between 0.05 and 0.0005.

27. Polymer according to claim 20, wherein the contacting/mixing and the heating executed using reactive extrusion.

28. Polyamide according to formula IV or IVa

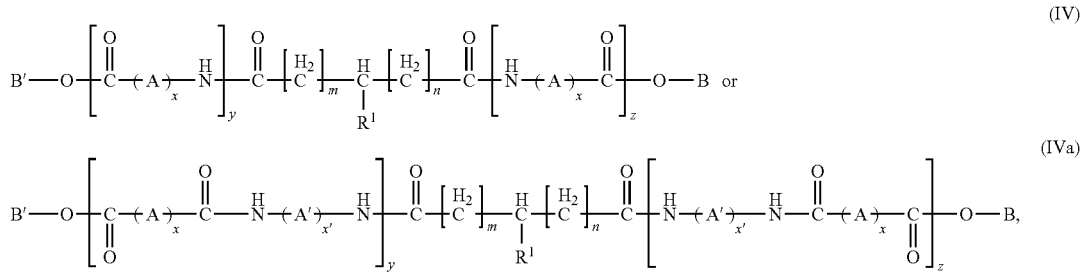

wherein
A is a divalent, branched or linear, saturated or non-saturated hydrocarbon chain, wherein optionally at least one hydrogen radical of the divalent, branched or linear, saturated or non-saturated hydrocarbon chain is replaced by F, Cl, Br, I, $NH_2$, SH or OH, with optionally one carbon atom of the divalent, branched or linear, saturated or non-saturated hydrocarbon chain being replaced by NH, O or S;

A' is a divalent, branched or linear, saturated or non-saturated hydrocarbon chain, wherein optionally at least one hydrogen radical of the divalent, branched or linear, saturated or non-saturated hydrocarbon chain is replaced by F, Cl, Br, I, $NH_2$, SH or OH, with optionally one carbon atom of the divalent, branched or linear, saturated or non-saturated hydrocarbon chain being replaced by NH, O or S;

B and B' independently from one another are selected from H or $C_{1-4}$-Alkyl;

x is a natural number between 1 and 24;
x' is a natural number between 1 and 24;
y is a natural number $\geq 1$;
z is a natural number $\geq 1$ or 0;
m and n are independently from each other selected from 0 and a natural number between 1 and 9 and n +m is a natural number between 1 and 9; and
$R^1$ is any radical;
with the proviso that $R^1$ may not be methyl.

29. Polyamide according to claim 28, wherein the polyamide is of formula V

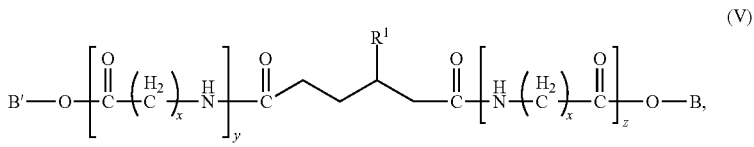

wherein
B and B' independently from one another are selected from H or C1-4-alkyl;
x is a natural number between 1 and 24;
y is a natural number $\geq 1$;
z is a natural number $\geq 1$ or 0;
$R^1$ is selected from the group consisting of halogen; a branched or linear, saturated or non-saturated, optionally substituted $C_{1-6}$ aliphatic radical; an optionally substituted aryl; a saturated or non-saturated, optionally substituted $C_{3-10}$-cycloalkyl; and an optionally substituted heterocyclyl.

30. Polyamide according to claim 29, wherein
x is 11;
and
$R^1$ is tertiary butyl.

31. A process using the polymer according to claim 28 in the production of implants or medical devices selected from balloon/balloon material, of stents, stent grafts, grafts graft connectors or catheters, comprising:
providing a polymer according to claim 28; and
producing at least one of an implant or a medical device selected from the group consisting of balloon/balloon material, stents, stent grafts, grafts, graft connectors, catheters, and combinations thereof.

32. Process for producing of a polymer, comprising:
(i) contacting/mixing the polyamide of claim 28 with an at least mono-substituted α,ω-di-carboxylic acid, and (ii) heating to a temperature above 150° C.

33. Process according to claim 32, wherein the at least mono-substituted α,ω-di-carboylic acid is added in an amount resulting in a molar ratio between the acid and the polyamide calculated relatively based on the equivalent number of lactam Units in the polyamide between 0.05 and 0.0005;
 or in an amount resulting in a molar ratio between the acid and the polyamide calculated relatively based on molecular weight of the polymerized amide building block

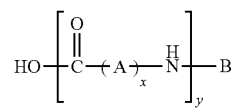

between 0.05 and 0.0005.

34. Process according to claim 33, wherein the one or more polyamide/s is contacted/mixed with the at least mono-substituted α,ω-di-carboylic acid, and then heated to a temperature above 150° C. in a reaction using reactive extrusion.

* * * * *